United States Patent
Copland

(10) Patent No.: US 8,919,956 B2
(45) Date of Patent: Dec. 30, 2014

(54) MODEL EYE PRODUCING A SPECKLE PATTERN HAVING A REDUCED BRIGHT-TO-DARK RATIO

(71) Applicant: AMO Wavefront Sciences, LLC., Albuquerque, NM (US)

(72) Inventor: Richard James Copland, Albuquerque, NM (US)

(73) Assignee: AMO Wavefront Sciences LLC., Santa Ana, CA (US)

(*) Notice: Subject to any disclaimer, the term of this patent is extended or adjusted under 35 U.S.C. 154(b) by 0 days.

(21) Appl. No.: 13/950,756

(22) Filed: Jul. 25, 2013

(65) Prior Publication Data

US 2014/0160428 A1 Jun. 12, 2014

Related U.S. Application Data

(62) Division of application No. 13/011,003, filed on Jan. 21, 2011, now Pat. No. 8,517,538.

(51) Int. Cl.
*A61B 3/10* (2006.01)
*A61B 3/00* (2006.01)
*G02B 27/48* (2006.01)

(52) U.S. Cl.
CPC ............. *A61B 3/0025* (2013.01); *A61B 3/1015* (2013.01); *G02B 27/48* (2013.01); *A61B 3/102* (2013.01)
USPC .......................................... 351/205; 351/246

(58) Field of Classification Search
USPC .......... 351/204, 205, 246; 359/455, 459, 599, 359/642, 647, 707, 708, 711; 250/552
See application file for complete search history.

(56) References Cited

U.S. PATENT DOCUMENTS

| 1,630,944 A | 5/1927 | Rose |
| 2,068,950 A | 1/1937 | Frederick |
| 3,598,470 A * | 8/1971 | Vetter ........................... 359/455 |
| 4,009,394 A * | 2/1977 | Mierzwinski ................. 250/552 |
| 4,253,743 A | 3/1981 | Matsumura |
| 5,042,938 A | 8/1991 | Shimozono |

(Continued)

FOREIGN PATENT DOCUMENTS

| DE | 102006025638 A1 | 12/2007 |
| DE | 102008055755 A1 | 5/2010 |

(Continued)

OTHER PUBLICATIONS

International Search Report for Application No. PCT/US2012/021979, mailed on Sep. 4, 2012, 6 pages.

*Primary Examiner* — Loha Ben
(74) *Attorney, Agent, or Firm* — AMO Wavefront Sciences LLC.

(57) ABSTRACT

A model eye includes an optically transmissive structure having a front curved surface to receive a coherent light beam, and an opposite rear planar surface for directing a portion of the coherent light beam back out the model eye through the front curved surface; and a material structure adhered to the rear planar surface of the optically transmissive structure that has a characteristic to cause a speckle pattern of the portion of the coherent light beam that is directed back out the front curved surface of the optically transmissive structure to have a bright-to-dark ratio of less than 2:1. In some embodiments, the material structure may include a fabric-reinforced polyethylene tape adhered to the rear planar surface of the optically transmissive structure by an adhesive. One example material structure which may be employed is duct tape.

14 Claims, 7 Drawing Sheets

(56) References Cited

U.S. PATENT DOCUMENTS

| | | |
|---|---|---|
| 6,485,142 B1 | 11/2002 | Sheehy et al. |
| 6,626,535 B2 | 9/2003 | Altmann |
| 6,802,609 B2 | 10/2004 | Mihashi et al. |
| 7,036,933 B2 | 5/2006 | Yamaguchi et al. |
| 7,425,067 B2 | 9/2008 | Warden et al. |
| 7,546,009 B2 * | 6/2009 | Kukulj et al. ............... 385/33 |
| 7,742,244 B2 | 6/2010 | Liu et al. |
| 7,792,249 B2 | 9/2010 | Gertner et al. |
| 8,128,262 B2 * | 3/2012 | Ramer et al. ............... 362/327 |
| 8,686,648 B2 * | 4/2014 | Ramer et al. ............... 315/185 S |
| 2002/0041359 A1 | 4/2002 | Mihashi et al. |
| 2003/0025877 A1 | 2/2003 | Yancey et al. |
| 2003/0174755 A1 | 9/2003 | Lai et al. |
| 2010/0002311 A1 | 1/2010 | Reichert |

FOREIGN PATENT DOCUMENTS

| | | |
|---|---|---|
| WO | 03049606 A2 | 6/2003 |
| WO | 2005047938 A2 | 5/2005 |
| WO | 2010086304 A1 | 8/2010 |

* cited by examiner

MODEL EYE PRODUCING A SPECKLE PATTERN HAVING A REDUCED BRIGHT-TO-DARK RATIO

This application is a divisional application and claims priority to U.S. application Ser. No. 13/011,003, entitled "Model Eye Producing a Speckle Pattern Having a Reduced Bright-To-Dark Ratio," filed on Jan. 21, 2011, now U.S. Pat. No. 8,517,538, the entire contents of which are hereby incorporated by reference in their entirety for all purposes as if fully set forth herein.

BACKGROUND AND SUMMARY

1. Field

This invention pertains to optical measurement equipment, and more particularly for a model eye for verifying proper operation and performance of optical measurement equipment, and a method for verifying proper operation and performance of optical measurement equipment with a model eye.

2. Description

There are a number of optical measurement or analysis instruments which utilize one or more light spots generated from coherent light sources, such as lasers or superluminscent laser diodes (SLDs), to make optical measurements of the eye. Well-known examples of such instruments include wavefront aberrometers (e.g., Shack-Hartmann wavefront aberrometers) and corneal topographers.

An undesirable feature of these light sources is that the light pattern produced in the instrument is marred by speckle. Speckle is a spotty pattern with large light intensity variations. FIG. 1 illustrates an example of a speckle pattern. Speckle is caused when the layer from which the light is scattered is thinner than the coherence length of the light source. A typical SLD has a bandwidth of thirty nanometers, which corresponds to a coherence length of one hundred microns.

Speckle can cause problems with some optical measurement or analysis instruments. For example, there are two ways that speckle causes measurement errors in an instrument that employs a Shack-Hartmann wavefront sensor. One problem is that the mathematical algorithms called reconstructors that are employed by such instruments have fitting errors in data sets that contain dark regions of the speckle pattern. Another problem is "intensity coupling." Intensity coupling may occur when a wavefront sensor is constructed such that the lenslet array is not located exactly one focal length from the pixel array. In that case, intensity variations cause shifts in the spot locations that are independent of the slope of the wavefront. These shifts cause errors in the calculated wavefront.

With the human eye, speckle is mitigated because the scattering occurs in a volume that has a thickness that is longer than the coherence length of the light source. The light penetrates into a layer of the eye and weak scatter occurs throughout the volume. As a result, when an SLD light source illuminates a human eye, the bright-to-dark ratio is typically about two to one.

Meanwhile, it is sometimes necessary to be able to verify correct operation and specified performance of an optical measurement instrument such as a wavefront aberrometer in an operational setting. In many instances, this is done by operating the measurement instrument to make a measurement of a model eye whose characteristics are known. In that case, typically the optical measurement instrument injects a probe beam into a front surface of the model eye. Light scatters from the back surface of the model eye similarly to the way it does with a human eye, and some of the scattered light travels back out of the front surface and into the optical measurement instrument.

However, when a typical model eye is measured, the speckle is more severe than is typically seen with a human eye. The problem is made even worse by the fact that the "cornea" of the model eye acts like a magnifying glass and makes the structure of the bright spots and dark regions appear large on the detector inside the optical measurement instrument. The typical speckle pattern for a model eye has a bright-to-dark ratio of twenty-to-one, which is about an order or magnitude greater than for a human eye. These large variations in light level make for inaccurate measurements, for the reasons explained above.

Therefore, it would be desirable to provide a model eye which produces a speckle pattern exhibiting a reduced bright-to-dark ratio.

In one aspect of the invention, a method comprises: providing a model eye comprising an optically transmissive structure having a front curved surface and an opposite rear planar surface, and a material structure adhered to the rear planar surface of the optically transmissive structure; directing a coherent light beam through the front curved surface of the optically transmissive structure to the opposite rear planar surface; receiving at a measurement instrument a portion of the light returned from the rear planar surface of the optically transmissive structure, wherein the material structure has a characteristic to cause the light received by the measurement instrument from the rear planar surface of the optically transmissive structure to have a speckle pattern with a bright-to-dark ratio of less than 2:1.

In another aspect of the invention, a model eye comprises: an optically transmissive structure having a front curved surface configured to receive a coherent light beam and an opposite rear planar surface for directing a portion of the coherent light beam back out the model eye through the front curved surface; and a material structure adhered to the rear planar surface of the optically transmissive structure and having a characteristic to cause a speckle pattern of the portion of the coherent light beam that is directed back out the front curved surface of the optically transmissive structure to have a bright-to-dark ratio of less than 2:1.

In yet another aspect of the invention, a model eye includes: an optically transmissive structure having a front curved surface and an opposite rear planar surface; and a fabric-reinforced polyethylene pressure-sensitive tape with a semi-flexible shell adhered to the rear planar surface of the optically transmissive structure by a pressure sensitive adhesive.

DETAILED DESCRIPTION

Exemplary embodiments of model eyes and methods for verifying proper operation and performance of optical measurement equipment through use of a model eye will be described in some detail below so as to illustrate various aspects and advantages of these devices and methods. However, it should be understood that the principles involved in these devices and methods can be employed in a variety of other contexts, and therefore the novel devices and method disclosed and claimed here should not be construed as being limited to the example embodiments described below.

Figure 1:
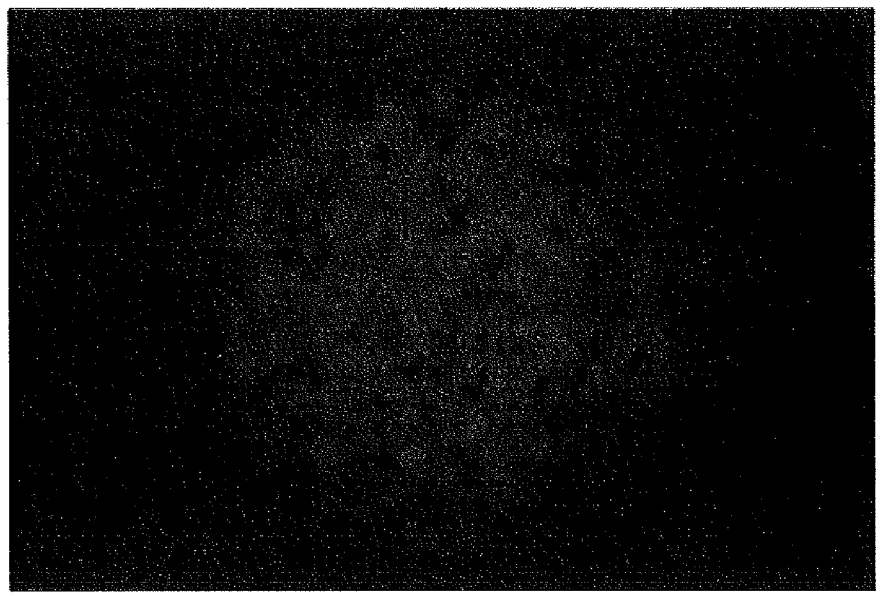
FIG. 1 illustrates an example of a speckle pattern.
Figure 2:
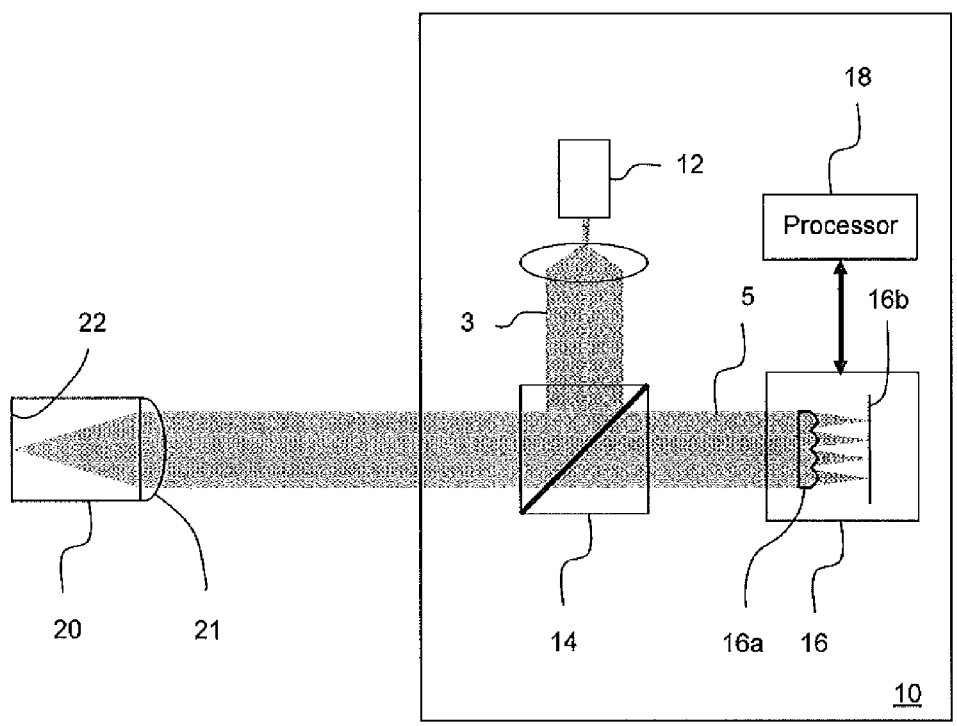
FIG. 2 illustrates an example of an optical measurement instrument making a measurement with one example embodiment of a model eye to verify correct operation and specified performance of the optical measurement instrument.

FIG. 2 illustrates an example of an optical measurement instrument 10 making a measurement with one example embodiment of a model eye 20 to verify correct operation and specified performance of an optical measurement instrument. Here optical measurement instrument 10 may be a wavefront aberrometer. Optical measurement instrument 10 includes, among other elements, a coherent light source (e.g., a laser or SLD) 12, a beamsplitter 14, a wavefront sensor 16, and a processor 18. In some embodiments wavefront sensor 16 may be a Shack-Hartmann wavefront sensor including a lenslet array 16a and a pixel array 16b (e.g., camera, charge-coupled-device (CCD) or CMOS array). In various embodiments, optical measurement instrument 10 may include a variety of other elements not shown in FIG. 1, such as optical elements (e.g., lenses, mirrors, etc.), a fixation target, aperture stops, etc. Model eye 20 has a front surface 21 and a rear or back surface 22. Front surface 21 may be curved to focus light onto rear surface 22 such that front surface 21 acts as a "lens" for model eye 20, and rear surface 22 acts as a "retina" for model eye 20.

To verify that optical measurement instrument 10 is performing correctly, coherent light source 12 generates a probe beam 3 which is injected into front surface 21 of model eye 20. Light scatters from rear surface 22 of model eye 20 and some of the scattered light travels back out of front surface 21 and into optical measurement instrument 10 as a return beam 5. Return beam 5 is provided to wavefront sensor 16 which can operate with processor 18 to make one or more measurements of one or more characteristics of model eye 20. The measurement(s) can be compared with known or previously measured characteristics of model eye 20 to allow a determination to be made as to whether optical measurement instrument 10 is operating correctly and/or within its specified performance tolerances.

As noted above, in general return beam 5 will exhibit a speckle pattern with some bright-to-dark ratio. If the bright-to-dark ratio of the speckle pattern is too great, then the measurement(s) of model eye 20 may be subject to error that may make it difficult to impossible to verify proper operation of optical measurement instrument 10.

Various techniques may be employed to address the problem of a speckle pattern whose bright-to-dark ratio is too great. The exterior of rear surface 22 of model eye 20 may be painted to make the reflectivity approximate that of the human eye. However it has been observed that generally, a painted surface also causes excessive speckle. Another solution is simply to turn up the power on light source 12 so the dark regions at least get some light. However, this does not solve the problem of calculated wavefront errors caused by intensity coupling as described above. Another solution is to send probe beam 3 through a rotating disk that moves the beam slightly on back surface 22 of model eye 20 during the time that pixel array 16b of wavefront sensor 16 is acquiring an image. This moves the speckle pattern around during the acquisition and fills in the dark regions. However, this adds complexity to the system. Another similar solution is to move back surface 22 of model eye 20 slightly during the acquisition time. This can be done by gently tapping on model eye 20. However that is not a practical solution for many reasons. Another possibility is to vibrate model eye 20 by some more controlled means, such as with an ultrasonic transducer. However that would require an energy source for model eye 20, such as a battery, again adding complexity to the system.

Figure 3A:
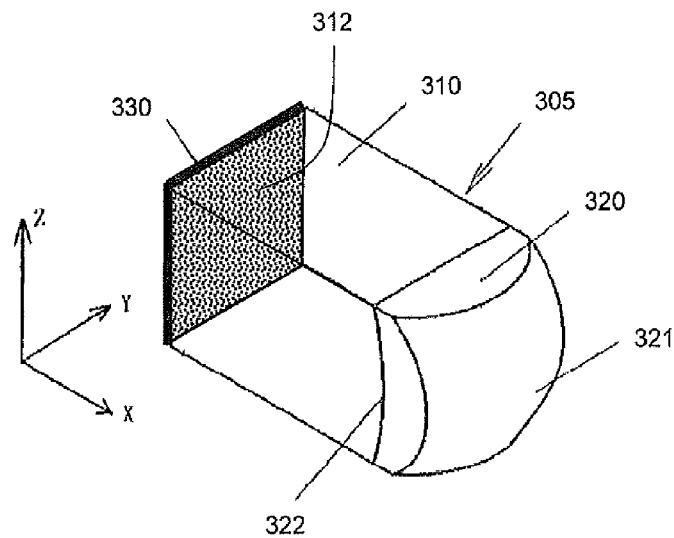
FIGS. 3A-3B illustrate one example embodiment of a model eye.
Figure 3B:
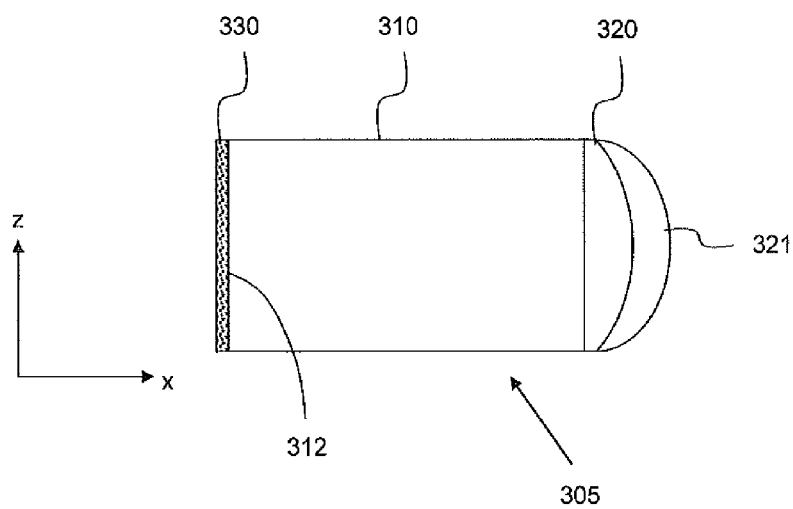

FIGS. 3A-3B illustrate one example embodiment of a model eye 300 that can produce a speckle pattern with a reduced bright-to-dark ratio. Model eye 300 includes an optically transmissive structure 305 having a front surface 321 and an opposite rear or back surface 312; and a material structure 330 adhered to rear surface 312 of optically transmissive structure 305.

Front surface 321 may be curved to focus light onto the opposite rear surface 312, which may be planar, such that front surface 321 acts as a "lens" for model eye 300, and rear surface 312 acts as a "retina" for model eye 300.

In some embodiments, optically transmissive structure 305 may comprise glass or a transparent polymer. In model eye 300, optically transmissive structure 305 includes a first plano-cylindrical portion 310 and a second sphero-cylindrical portion 320 which meet at a plano interface 322. In optically transmissive structure 305, first plano-cylindrical portion 310 and second sphero-cylindrical portion 320 may be formed as a unitary structure, or may comprise two separate structures joined together at plano interface 322. Also, in other embodiments the optically transmissive structure of a model eye may have a different shape, for example a cylindrical structure with a circular cross-section instead of the rectangular or square cross-section of optically transmissive structure 305.

When used to verify the proper operation of an optical measurement instrument (e.g., optical measurement instrument 10), front curved surface 321 of optically transmissive structure 305 receives a coherent light beam and provides it to the opposite rear surface 312, and rear surface 312 directs a portion of the coherent light beam back out through front surface 321.

Beneficially, material structure 330 has a characteristic to cause a speckle pattern of the portion of the coherent light beam that is directed back out front surface 321 of optically transmissive structure 310 to have a reduced bright-to-dark ratio compared to the bright-to-dark ratio of the speckle pattern that is produced in the absence of material structure 330. Beneficially, material structure 330 has a characteristic to cause a speckle pattern of the portion of the coherent light beam that is directed back out front surface 321 of optically transmissive structure 310 to have a bright-to-dark ratio of less than 2:1.

FIGS. 4A-4E illustrate some example embodiments of the material structure 330 of FIGS. 3A-B.

Figure 4A:
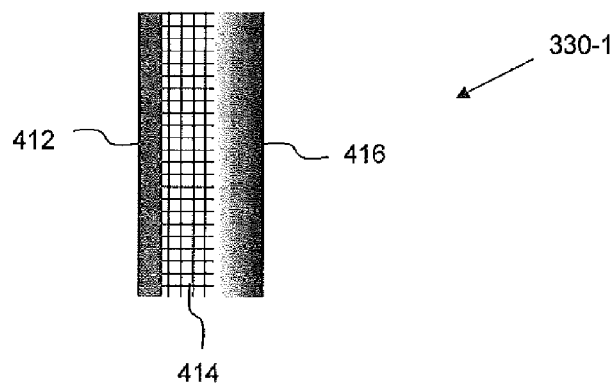
FIGS. 4A-4E illustrate some example embodiments of a material structure that may be applied to a back surface of an optically transmissive structure of a model eye.

FIG. 4A illustrates a first embodiment 330-1 of material structure 330 comprising a piece of duct tape.

Generally speaking, duct tape is a fabric-reinforced polyethylene pressure-sensitive tape with a semi-flexible shell and a pressure-sensitive adhesive. Duct tape was first marketed around 1942 and its first large scale use was by the U.S. military, for example to keep moisture out of ammunition cases. Commonly, duct-tape construction consists of a polyisoprene-based adhesive 412, a fabric (scrim) reinforcement 414, and a polyethylene backing 416.

Surprisingly, the inventor has discovered that by adhering a piece of duct tape to the rear surface of the optically transmissive structure of a model eye, the speckle pattern of the light returned from the rear surface of the optically transmissive structure and back out the front surface of the optically transmissive structure has a speckle pattern which exhibits a reduced bright-to-dark ratio compared to the same model eye without the duct tape. In some embodiments, the speckle pattern exhibits a bright-to-dark ratio of less than or equal to 2:1. In some embodiments, so-called gaffer tape may be employed in lieu of duct tape.

Figure 4B:
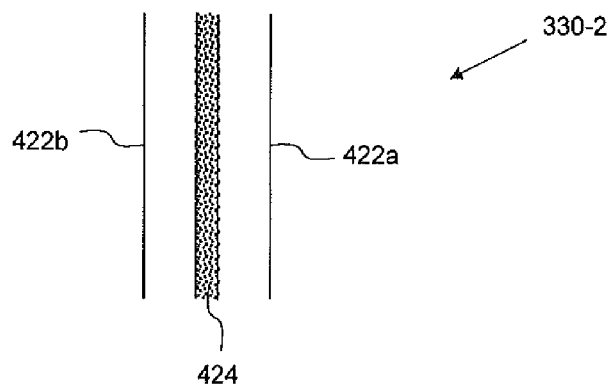

FIG. 4B illustrates a second embodiment 330-2 of material structure 330 comprising at least two layers 422a & 422b of optically transmissive adhesive tape with a material 424 having a plurality of light scattering particles disposed between the at least two layers of optically transmissive adhesive tape. By adhering material structure 330-2 to the rear surface of the optically transmissive structure of a model eye, the speckle pattern of the light returned from the rear surface of the optically transmissive structure and back out the front surface of the optically transmissive structure has a speckle pattern which exhibits a reduced bright-to-dark ratio compared to the same model eye without material structure 330-2. In some embodiments, the speckle pattern exhibits a bright-to-dark ratio of less than or equal to 2:1.

Figure 4C:
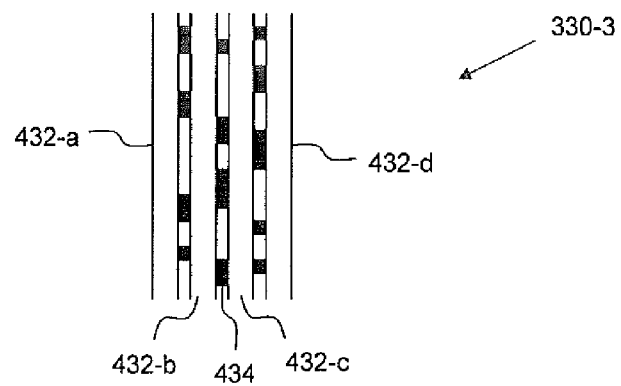

FIG. 4C illustrates a third embodiment 330-3 of material structure 330 comprising a plurality of layers 432a, 432b, 432c & 432d of optically transmissive adhesive tape with a plurality of pencil or graphite marks 434 on each successive layer of the optically transmissive adhesive tape. By adhering material structure 330-3 to the rear surface of the optically transmissive structure of a model eye, the speckle pattern of the light returned from the rear surface of the optically transmissive structure and back out the front surface of the optically transmissive structure has a speckle pattern which exhibits a reduced bright-to-dark ratio compared to the same model eye without material structure 330-3. In some embodiments, the speckle pattern exhibits a bright-to-dark ratio of less than or equal to 2:1.

Figure 4D:
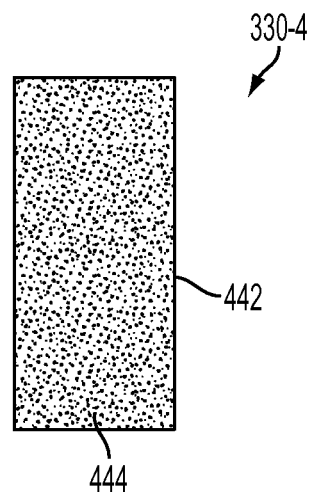

FIG. 4D illustrates a fourth embodiment 330-4 of material structure 330 comprising a layer of optically transmissive paint 442 with light scattering particles 444 embedded within. By adhering material structure 330-4 to the rear surface of the optically transmissive structure of a model eye, the speckle pattern of the light returned from the rear surface of the optically transmissive structure and back out the front surface of the optically transmissive structure has a speckle pattern which exhibits a reduced bright-to-dark ratio compared to the same model eye without material structure 330-4. In some embodiments, the speckle pattern exhibits a bright-to-dark ratio of less than or equal to 2:1.

Figure 4E:
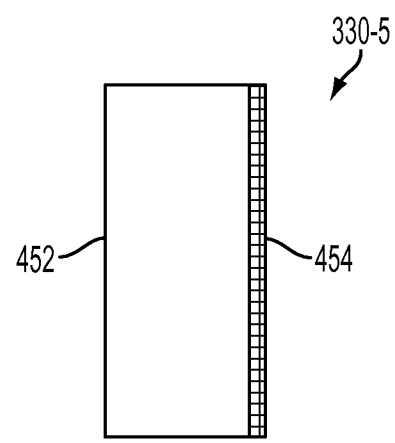

FIG. 4E illustrates a fifth embodiment 330-5 of material structure 330 comprising a caulking material 452 with a gauze material 454 applied thereto. By adhering material structure 330-5 to the rear surface of the optically transmissive structure of a model eye, the speckle pattern of the light returned from the rear surface of the optically transmissive structure and back out the front surface of the optically transmissive structure has a speckle pattern which exhibits a reduced bright-to-dark ratio compared to the same model eye without material structure 330-5. In some embodiments, the speckle pattern exhibits a bright-to-dark ratio of less than or equal to 2:1.

Although FIGS. 4A-4E show various specific embodiments of material structures of material structure 330, it should be understood that other embodiments are possible. In some other embodiments, the material structure may be otherwise incorporated (e.g., painted, sprayed, extruded, thermoformed, or the like) into the model eye such that the material structure is located at or on the rear surface of the optically transmissive structure of the model eye and provide the characteristic of causing the light received by the measurement instrument from the rear surface of the optically transmissive structure to have a speckle pattern with a reduced bright-to-dark ratio, and beneficially a bright-to-dark ratio of less than 2:1.

Figure 5:
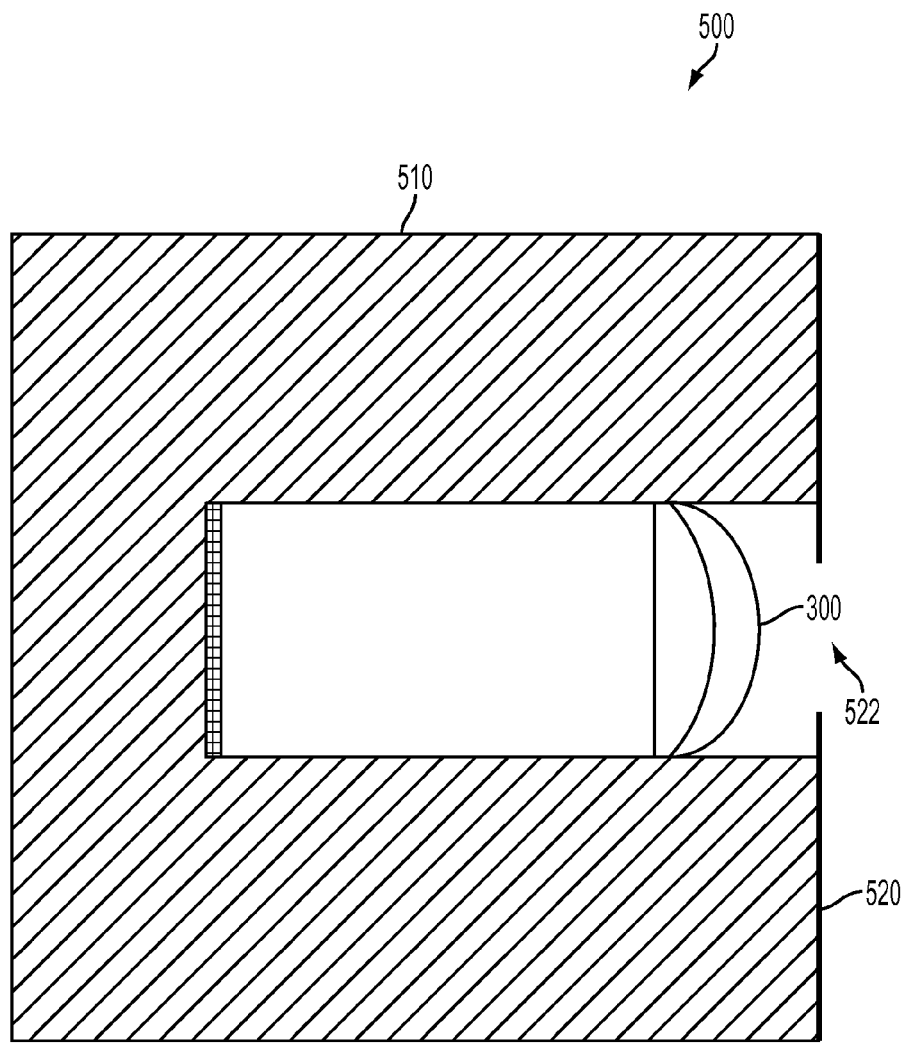
FIG. 5 illustrates another example embodiment of a model eye.

FIG. 5 illustrates another example embodiment of a model eye 500. Model eye 500 includes model eye 300 of FIGS. 3A-3B, together with a model eye holder or mount 510, and an opaque structure 520 having an aperture 522 therethrough disposed in front of the front surface of model eye 300. Opaque structure 520 may act as an "iris" for model eye 500. The operation of model eye 500 is similar to that of model eye 300 and so a description thereof will not be repeated.

Figure 6:
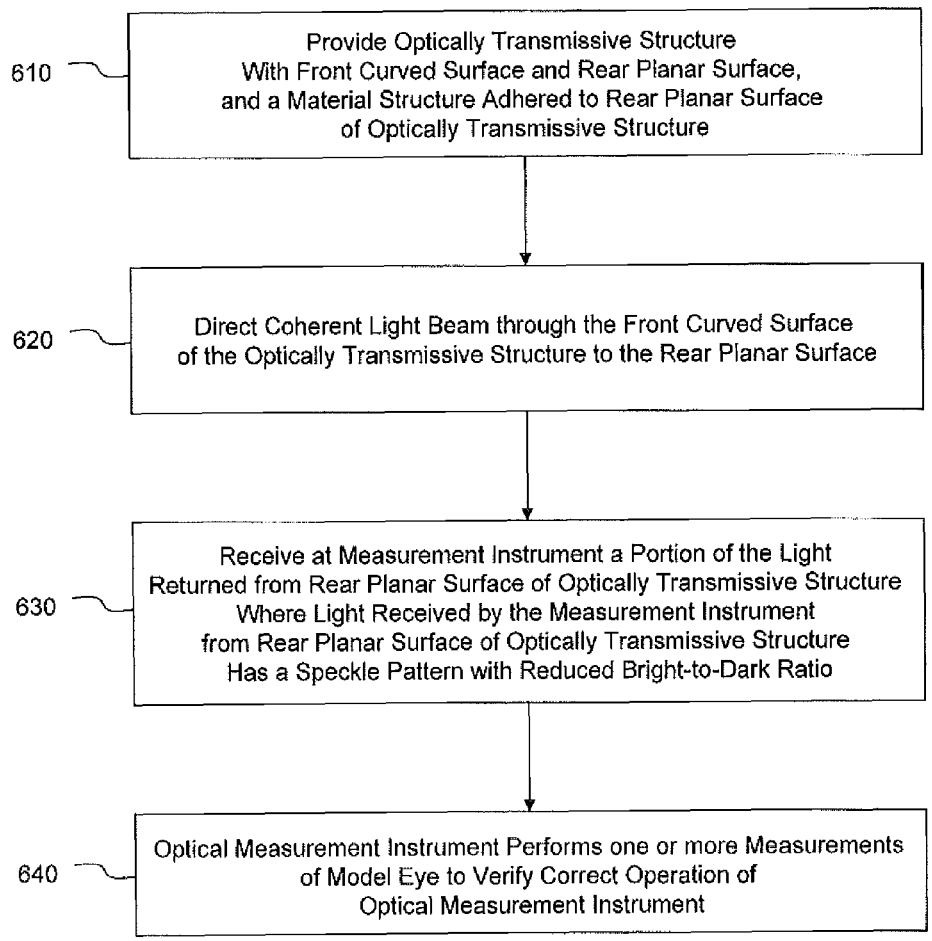
FIG. 6 is a flowchart of an example embodiment of a method for verifying proper operation and performance of optical measurement equipment.

FIG. 6 is a flowchart of an example embodiment of a method 600 for verifying proper operation and performance of optical measurement equipment.

In operation 610, a model eye is provided as an optically transmissive structure with a front curved surface and a rear planar surface, and a material structure adhered to the rear planar surface of the optically transmissive structure. The model eye may be model eye 300 or model eye 500, and the material structure may be material structure 330, including for example any of the embodiments shown in FIGS. 4A-4E.

In operation 620, a coherent light beam is directed through the front curved surface of the optically transmissive structure to the opposite rear planar surface.

In operation 630, a measurement instrument receives a portion of the light returned from the rear planar surface of the optically transmissive structure. The material structure has a characteristic to cause the light received by the measurement instrument from the rear planar surface of the optically transmissive structure to have a speckle pattern with a reduced bright-to-dark ratio, and beneficially a bright-to-dark ratio of less than 2:1.

In operation 640, the optical measurement instrument performs one or more measurements of the model eye to verify correct operation of the optical measurement instrument, for example by comparing the measurement result(s) to known parameters of the model eye.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

I claim:

1. A model eye, comprising:
    an optically transmissive structure having a front curved surface configured to receive a coherent light beam and an opposite rear planar surface for directing a portion of the coherent light beam back out of the model eye through the front curved surface; and
    a material structure adhered to the rear planar surface of the optically transmissive structure and having a characteristic to cause a speckle pattern of the portion of the coherent light beam that is directed back out of the front curved surface of the optically transmissive structure to have a bright-to-dark ratio of less than 2:1.

2. The model eye of claim 1, wherein the material structure comprises a fabric-reinforced polyethylene pressure-sensitive tape adhered to the rear planar surface of the optically transmissive structure by an adhesive.

3. The model eye of claim 1, wherein the material structure comprises at least two layers of optically transmissive adhesive tape with a material having a plurality of light scattering particles disposed between the at least two layers of optically transmissive adhesive tape.

4. The model eye of claim 1, wherein the material structure comprises a plurality of layers of optically transmissive adhesive tape with a plurality of pencil marks on each successive layer of the optically transmissive adhesive tape.

5. The model eye of claim 1, wherein the material structure comprises a layer of optically transmissive paint with light scattering particles embedded within.

6. The model eye of claim 1, wherein the material structure comprises a caulking material with a cloth material applied thereto.

7. A model eye, comprising:
   an optically transmissive structure having a front curved surface and an opposite rear planar surface; and
   a tape adhered to the rear planar surface of the optically transmissive structure by a pressure sensitive adhesive.

8. The model eye of claim 7, further comprising an opaque structure having an aperture therethrough disposed on an opposite side of the front curved surface of the optically transmissive structure as the rear planar surface of the optically transmissive structure.

9. The model eye of claim 7, wherein the optically transmissive structure comprises glass or a transparent polymer.

10. The model eye of claim 7, wherein the tape comprises a fabric-reinforced polyethylene tape with a pressure-sensitive adhesive.

11. The model eye of claim 7, wherein the tape comprises duct tape.

12. The model eye of claim 7, wherein the tape comprises gaffer tape.

13. The model eye of claim 7, wherein the tape is a latex tape.

14. The model eye of claim 7, further comprising a holder having an opening therein defining a sleeve configured to hold the optically transmissive structure.

* * * * *